United States Patent [19]

Barton

[11] Patent Number: 5,114,964

[45] Date of Patent: * May 19, 1992

[54] ARYL-SUBSTITUTED BENZOCYCLOALKYL-DERIVED ANTI-ATHEROSCLEROTIC AGENTS

[75] Inventor: Jeffrey N. Barton, Philadelphia, Pa.

[73] Assignee: Rhone-Poulenc Rorer Pharmaceuticals Inc., Collegeville, Pa.

[*] Notice: The portion of the term of this patent subsequent to Sep. 5, 2006 has been disclaimed.

[21] Appl. No.: 461,198

[22] Filed: Jan. 5, 1990

Related U.S. Application Data

[63] Continuation-in-part of Ser. No. 431,417, Nov. 3, 1989, Pat. No. 4,946,860.

[51] Int. Cl.$^5$ .................. A61K 31/35; C07D 309/30
[52] U.S. Cl. ........................... 514/460; 549/292
[58] Field of Search .................. 514/460; 549/292

[56] References Cited

U.S. PATENT DOCUMENTS

| | | | |
|---|---|---|---|
| 4,499,289 | 2/1985 | Baran | 549/292 |
| 4,804,679 | 2/1989 | Anderson | 514/460 |
| 4,863,957 | 9/1989 | Neuenschwander | 514/460 |
| 4,892,884 | 1/1990 | Neuenschwander | 514/460 |

Primary Examiner—Mary C. Lee
Assistant Examiner—Jacqueline Haley
Attorney, Agent, or Firm—Raymond S. Parker; Martin F. Savitzky

[57] ABSTRACT

Disclosed are novel aryl-substituted benzocycloalkyl-derived 3-hydroxy-3-methylglutaryl-coenzyme A reductase inhibitors useful as antihypercholesterolemic agents represented by the formula:

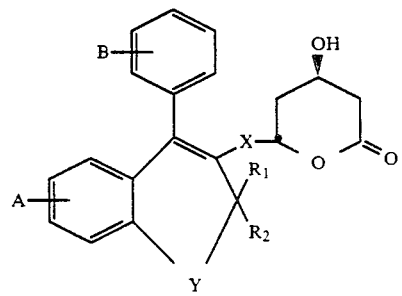

their corresponding dihydroxy acids, and pharmaceutically acceptable salts thereof.

5 Claims, No Drawings

ARYL-SUBSTITUTED BENZOCYCLOALKYL-DERIVED ANTI-ATHEROSCLEROTIC AGENTS

This invention is a continuation-in-part of Ser. No. 431,417 filed on Nov. 3, 1989 now U.S. Pat. No. 4,946,860.

BACKGROUND OF THE INVENTION

1. Field of the Invention

The present invention relates to compounds, pharmaceutical compositions and a method useful for reducing serum cholesterol in humans. More particularly, the invention relates to aryl-substituted benzocycloalkyl-derived compounds and pharmaceutically acceptable salts thereof which are potent inhibitors of the enzyme 3-hydroxy-3-methylglutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Reported Developments

Inhibitors of HMG-CoA reductase are effective in lowering blood plasma cholesterol level as well as inhibiting the biosynthesis of cholesterol in humans. As such, inhibitors of HMG-CoA reductase are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)-alkyl]-4-hydroxy-pyran-2-ones useful as hypocholesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-etherified-hydroxy-2', 6'-dimethylpolyhydro-1'-naphthyl)ethyl]-4(R)-hydroxy-3,4,5,6-tetrahydro-2H-pyran-2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4'-fluoro-3,3',5-trimethyl[1,1'-biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

SUMMARY OF THE INVENTION

The present invention comprises benzocycloalkenyl derivatives of the formula

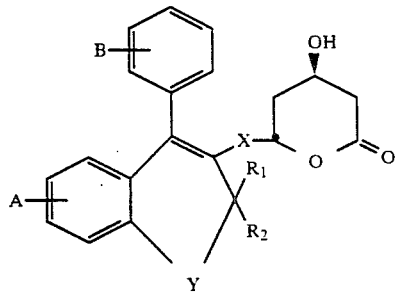

wherein:
- A is H, alkyl or alkoxy;
- B is H, alkyl, alkoxy, halo or $CF_3$;
- X is $CH_2CH_2$ or $CH=CH$;
- Y is $CH_2$, $CH_2CH_2$ or $CH=CH$;
- $R_1$ and $R_2$ are independently H, alkyl, hydroxyalkyl, halo or $CF_3$;

their corresponding dihydroxy acids; and pharmaceutically acceptable salts thereof.

The invention also comprises pharmaceutical compositions comprising the aforesaid compounds useful for reducing serum cholesterol in humans.

Another aspect of this invention comprises a method for inhibiting cholesterol biosynthesis in humans by administering an aforesaid compound or composition.

DETAILED DESCRIPTION OF THE INVENTION

As employed above and throughout the specification, the following terms, unless otherwise indicated, shall be understood to have the following meaning: "Alkyl" means a saturated or unsaturated aliphatic hydrocarbon which may be either straight- or branched-chained containing from about one to about ten, and preferably one to six carbon atoms.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl and 3-hydroxypropyl.

"Alkoxy" means an alkyl-oxy group in which alkyl is as previously described. Lower alkoxy groups are preferred. Exemplary groups include methoxy, ethoxy, n-propoxy, i-propoxy and n-butoxy.

"Halo" means Cl, F, Br and I.

The compounds of this invention may be useful in the form of the free acid, in the form of salts and as a hydrate. All forms are within the scope of the invention.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.

A reaction scheme procedure for preparing the compounds of the present invention is as shown:

Reaction Scheme

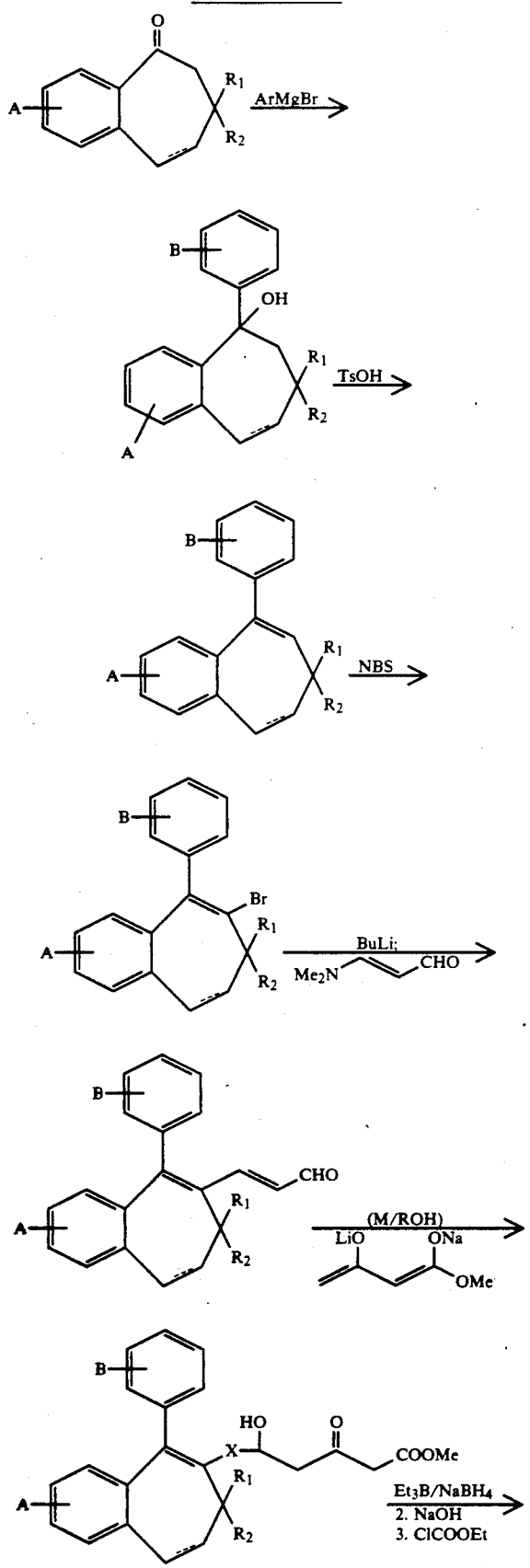

-continued
Reaction Scheme

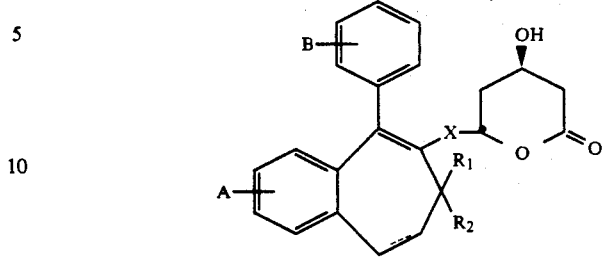

A = H, alkyl, alkoxy
B = H, alkyl, alkoxy, halo, CF$_3$
X = CH$_2$CH$_2$, CH=CH
optional double bond The starting materials may be obtained from chemical supply houses, such as the Aldrich Chemical Co. but they may also be synthesized in accordance with methods known in the art.

The following preparative example will further illustrate the invention.

EXAMPLE 1

A.

7,7-Dimethyl-9-(4-fluorophenyl)-5,6,8,9-tetrahydro-7H-benzocycloheptan-9-ol

To a stirred solution of 4-fluorophenylmagnesium bromide in THF (40 mL of 1.0M, 40 mmol) at 0° under nitrogen was added dropwise a solution of 4.65 g (30 mmol) of 7,7-dimethylbenzocycloheptan-5-one in 20 mL THF. After 1.5 hours at 0° C. the reaction was diluted with Et$_2$O and washed with dilute HCl, water and brine. Solvents were removed on a rotary evaporator and the crude mixture used directly.

B.

5,6-Dihydro-7,7-dimethyl-9-(4-fluorophenyl)-7H-benzocycloheptene

To the product of Example 1A was added 5.28 g (66.8 mmol) pyridine. The mixture was diluted with 50 mL CH$_2$Cl$_2$ and stirred in an ice bath while 2.5 mL (34.7 mmol) thionyl chloride was added dropwise. After 45 minutes the mixture was diluted with ether and washed with H$_2$O, dilute HCl and brine. The solvents were removed on a rotary evaporator and the crude product chromatographed on silica gel to give 5.0 g of a cloudy oil.

C.

5,6-Dihydro-8-bromo-7,7-dimethyl-9-(4-fluorophenyl)-7H-benzocycloheptene

The product of Example 1B (10.1 g, 37.9 mmol) was dissolved in 150 mL CH$_2$Cl$_2$ and stirred at room temperature. To this was added 8.41 g (47 mmol) NBS and the stirring continued for 2.5 days. At this point, a further 1.07 g (6 mmol) of NBS was added. After a further 6 hours, the mixture was concentrated, redissolved in Et$_2$O and filtered. The filtrate was concentrated to give a crude solid which was used directly.

D. 3-[5,6-Dihydro-7,7-dimethyl-9-(4-fluorophenyl)-7H-benzocyclohepten-8-yl]-2-propenal A solution of the crude bromide of Example 1C (3.46 g, 10 mmol) in 30 mL THF was stirred with 0.3 g 60% NaH for 15 minutes at room temperature under nitrogen, then cooled to −78° C. To this was added dropwise 4.4 mL of 2.5BuLi (11 mmol). A dark red color formed slowly. A solution of 1.16 g (11.7 mmol) 3-(dimethylamino)acrolein in 2 mL THF was added dropwise and the mixture allowed to warm slowly to 0° C. After a total of 1 hour the reaction was quenched with 2 mL $H_2O$ and concentrated. Chromatography of the crude product on silica gel gave 1.08 g of the aldehyde.

E. Methyl 6(E)-7-[5,6-dihydro-7,7-dimethyl-9-(4-fluorophenyl)-7H-benzocyclohepten-8-yl]-5-hydroxy-3-oxo-6-heptenoate To a suspension of 0.61 g (15 mmol) of 60% NaH in 10 mL THF, stirred at −10° C. under nitrogen, was added dropwise a solution of 1.23 g (10.6 mmol) methyl acetoacetate in 5 mL THF. When gas evolution had ceased, the mixture was cooled to −20° C. and 3.5 mL of 2.5M BuLi (8.8 mmol) was added dropwise. Concurrently the aldehyde of Example 1D (1.08 g, 3.37 mmol) was dissolved in 5 mL THF and stirred with a small quantity of NaH. The dianion solution was allowed to reach −10° C. and the aldehyde solution then was added dropwise. After 5 minutes the reaction was partitioned between $Et_2O$ and 2N HCl. The organic layer was washed with $H_2O$ and brine and concentrated. Chromatography over silica gel using increasing concentrations of EtOAc in hexanes gave 0.76 g of the desired adduct as an orange oil.

F. Methyl 6(E)-3,5-syn-7-[5,6-dihydro-7,7-dimethyl-9-(4-fluorophenyl)-7H-benzocyclohepten-8-yl]-3,5-dihydroxy-6-heptenoate The ketoester of Example 1E (0.76 g, 1.74 mmol) was dissolved in 5 mL THF and treated successively with ca. 5 mg tBuCOOH and 2.5 mL 1M $Et_3B$. After 1.5 hours at room temperature the solution was cooled to −78° C. and 41 mg (1.08 mmol) $NaBH_4$ was added. Immediately 2 mL MeOH was added dropwise. The reaction was stirred for 15 minutes at −78° C., warmed slowly to −20° C., and quenched with 5 mL 10% $H_2O_2$. The mixture was stirred at 0° C. until the exothermic reaction was over, then diluted with $Et_2O$ and washed several times with $H_2O$ and brine. Concentration of the organic layer gave crude diol which was used directly.

G. Trans-(E)-6-[2-[5,6-dihydro-7,7-dimethyl-9-(4-fluorophenyl)-7H-benzocyclohepten-8-yl]ethenyl]-4-hydroxy-3,4,-5,6-tetrahydro-2H-pyran-2-one A solution of the crude diol from Example 1F (1.74 mmol) in 10 mL MeOH was treated with 2 mL 10% aqueous NaOH. When TLC indicated complete hydrolysis (2 hours) the mixture was quenched with dilute HCl and extracted with several portions of 4:1 hexanes:EtOAc. The extracts were concentrated and redissolved in 15 mL $CH_2Cl_2$. To this was added 0.28 g (2.8 mmol) of triethylamine. The solution was stirred in an ice bath while a solution of 0.23 g (2.12 mmol) ethyl chloroformate in 5 mL $CH_2Cl_2$ was added dropwise. After 15 minutes, TLC indicated complete reaction. The mixture was washed with dilute HCl and $H_2O$ and concentrated. Chromatography on silica gel using hexanes/EtOAc gave 150 mg. of product as a thick oil. m/e 406.1920 (Calc for $C_{26}H_{27}FO_3$ 406.1932)

EXAMPLE 2

A. 5-Bromo-7,7-dimethyl-9-(4-fluorophenyl)-7H-benzocycloheptene

The bromide of Example 1C (9.87 g, 28.5 mmol) was dissolved in 120 mL $CCl_4$. To this was added 7.92 g (44.2 mmol) NBS, followed by ca. 0.1 g benzoyl peroxide. The mixture was heated to reflux until all NBS had reacted (2.5 hours), then cooled and filtered. The solvent was removed and the residue heated at reflux with 8.12 g (53.4 mmol) DBU in 100 mL toluene for 2 hours. The cooled mixture was washed with water, dilute HCl and brine, then filtered through a small plug of silica gel. Removal of solvent gave 9.3 g of diene which was used directly.

B. 3-[7,7-Dimethyl-9-(4-fluorophenyl-7H-benzocyclohepten-8-yl]-2-propenal

The diene of Example 2A (9.3 g, 27 mmol) was dissolved in 100 mL THF and 0.49 g 60% NaH was added. The suspension was stirred at room temperature for 30 minutes under nitrogen, then cooled to −78° C. and treated dropwise with 14 mL of 2.5M BuLi (35 mmol). The exchange was allowed to proceed for 15 minutes. A solution of 4.55 g (45.9 mmol) 3-(dimethylamino)acrolein in 20 mL THF was then added dropwise and the mixture allowed to warm slowly. Upon reaching room temperature the reaction was quenched with 2 mL $H_2O$, diluted with ether, and washed exhaustively with $H_2O$. Concentration and chromatography of the product gave the desired aldehyde as an orange oil.

C. Methyl 6(E)-7-[7,7-dimethyl-9-(4-fluorophenyl)-7H-benzocyclohepten-8-yl]-5-hydroxy-3-oxo-6-heptenoate A dianion solution was prepared according to Example 1E from 0.68 g (5.86 mmol) of methyl acetoacetate and 2.0 mL of 2.5M BuLi (5 mmol). A solution of 0.82 g (2.58 mmol) of the enal of Example 2B in 4 mL THF was then added dropwise at −20° C. After 25 minutes, the reaction was worked up as previously described; chromatography on silica gel gave 1.5 g of keto ester which was used directly.

D. Methyl 6(E)-3,5-syn-7-[7,7-dimethyl-9-(4-fluorophenyl)-7H-benzocyclohepten-8-yl]-3,5-dihydroxy-6-heptenoate The above ketol in 20 mL THF was treated with 5 mL 1M $Et_3B$ (5 mmol) at room temperature under nitrogen. After 1.5 hours the solution was cooled to −78° C. and treated with 0.14 g (3.7 mmol) $NaBH_4$ and 4 mL MeOH according to Example 1F. Upon oxidative workup the mixture was stirred overnight and further processed as above. Concentration gave 1.52 g of crude diol which was used directly.

E.
6-(E)-3,5-syn-7-[7,7-dimethyl-9-(4-fluorophenyl)-7H-benzocyclohepten-8-yl]-3,5-dihydroxy-6-heptenoic acid The above diol was dissolved in 30 mL MeOH and treated with 15.3 g IRA-402 resin. After 75 minutes, the ester spot had disappeared by TLC. The mixture was filtered and the resin washed extensively with MeOH. The dried resin was resuspended in 30 mL EtOAc and treated with 2 mL HOAc. After 30 minutes the resin was filtered off and resubjected to fresh extraction. The combined filtrates were concentrated in vacuo to give 0.85 g of diol acid.

F.
Trans-(E)-6-[2-[7,7-dimethyl-9-(4-fluorophenyl)-7H-benzocyclohepten-8-yl]ethenyl]-4-hydroxy-3,4,5,6-tetrahydro-2H-pyran-2-one A solution of 0.84 g (1.99 mmol) of the acid of Example 2E in 20 mL $CH_2Cl_2$ was treated according to Example 1G with 0.31 g $Et_3N$ (3.1 mmol) and 0.25 g EtOCOCl (2.30 mmol). After 45 minutes, the reaction was worked up and chromatographed on silica gel. Product-rich fractions were combined and recrystallized from hexanes/EtOAc. The mother liquors were reprocessed as above to give a total of 200 mg lactone; m.p. 135°-140° C.

Employing the Reaction Scheme and using analogous procedures to that used in Example 1, the following compounds are prepared:

Trans-(E)-6-[2-[7,7-dimethyl-9-(3-methyl-4-fluorophenyl)-7H-benzocyclohepten-8-yl]ethenyl]-4-hydroxy-3,4,5,6-tetrahydro-2H-pyran-2-one;

Trans-(E)-6-[2-[7,7-dimethyl-3-methoxy-9-(3-methyl-4-fluorophenyl)-7H-benzocyclohepten-8-yl]ethenyl]-4-hydroxy-3,4,5,6-tetrahydro-2H-pyran-2-one;

Trans-(E)-6-[2-[7,7-dimethyl-9-(3,5-dimethylphenyl)-7H-benzocyclohepten-8-yl]ethenyl]-4-hydroxy-3,4,5,6-tetrahydro-2H-pyran-2-one;

Trans-(E)-6-[2-[5,6-dihydro-7,7-dimethyl-9-(3-methyl-4-fluorophenyl)-7H-benzocyclohepten-8-yl]ethenyl]-4-hydroxy-3,4,5,6-tetrahydro-2H-pyran-2-one;

Trans-6-[2-[7,7-dimethyl-9-(3-methyl-4-fluorophenyl)-7H-benzocyclohepten-8-yl]ethyl]-4-hydroxy-3,4,5,6-tetrahydro-2H-pyran-2-one; and Trans-(E)-6-[2-[4,7,7-trimethyl-9-(3-methyl-4-fluorophenyl)-7H-benzocyclohepten-8-yl]ethenyl]-4-hydroxy-3,4,-5,6-tetrahydro-2H-pyran-2-one.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations are to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course, be given in two to four divided doses. With other forms of administration equivalent or adjusted doses will be administered depending on the route of administration.

The utility of the claimed compounds is measured by the test methods described hereunder. The methods are based on the articles: "Purification of 3-Hydroxy-3-Methylglutaryl-Coenzyme A Reductase From Rat Liver" by Kleinsek et al., Proc. Natl. Acad. Sci. USA, Vol. 74, pp. 1431–1435, April 1977, Biochemistry; "Mevinolin: A Highly Potent Competitive Inhibitor of Hydroxy Methyl Glutaryl-Coenzyme A Reductase and a Cholesterol-Lowering Agent" by Alberts et al., Proc. Natl. Acad. Sci. USA, Vol. 77, pp. 3951–3961, July 1980, Biochemistry; "Effects of ML-236B on Cholesterol Metabolism in Mice and Rats: Lack of Hypocholesterolemic Activity in Normal Animals" by Endo et al., Biochemica et Biophysica Acta, 575 (1979) 266–276; and "Evidence of Regulation of 3-Hydroxy-3-Methylglutaryl Coenzyme A Reductase Activity and Cholesterol Synthesis in Nonhepatic Tissues of Rat" by Balasubramaniam et al., Proc. Natl. Acad. Sci. USA, Vol. 73, No. 8, pp. 2564–2568, Aug. 1976, Biochemistry.

The first method used (designated HMGR Screen) was as follows: Male rats were acclimated to an alternate 12 hour light-dark cycle for a period of 2-3 weeks. The animals, weighing 180-230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at −80° C. in 300 µl portion samples. Prior to use, the enzyme was activated at 37° C. for 30 minutes in a reaction mixture. The reaction mixture was contained in a volume of 240 µl:0.14M potassium phosphate buffer (pH 7.0); 0.18M KCl; 3.5 mM EDTA; 10 mM dithiothreitol; 0.1 mg/ml BSA; 30,000 cpm of [$^{14}$C]

HMG-CoA; 20 μM HMG-CoA; and 200 μg of solubilized enzyme with and without inhibitors (in 10 μl DMSO). After 5 minutes incubation at 37° C. the reaction was initiated with 0.2 mM NADPH. The final assay volume was 300 μl. After 10 minutes the reaction mixture was terminated with 100 μl of 1N HCl. After an additional incubation for 15 minutes at 37° C. to allow for complete lactonization of the product, the mixture was diluted with 3 ml GDW. The diluted mixture was then poured over a 0.7×1.4 cm column containing 100–200 mesh Bio-Rex ion-exchange resin (chloride form of Bio-Rad) which was equilibrated with distilled water. With this resin the unreacted [$^{14}$C] HMG-CoA was adsorbed and the product [$^{14}$C] lactone was eluted (80% recovery) directly into scintillation vials. After the addition of 10 ml of Aquasol, radioactivities of the samples were measured in a scintillation counter. The compound of Example 1G showed an IC$_{50}$ value of 16 nM per liter, while the compound of Example 2E showed an IC$_{50}$ value of 6.9 nM per liter.

The second method used (designated Ex-Vivo Non-Fasted and Ex-Vivo Fasted) used was as follows: Rats of 170–210 g were maintained on a low cholesterol diet for one week prior to use. Drugs were given orally in 0.5% methocel to both fed and fasted (fasted for 16 hours) rats. After one hour (fasted rats) and two hours (fed rats) the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium acetate (2 μCi, 1 mM). The tubes were gassed with 95% O$_2$/5%CO$_2$, capped and incubated at 37° C. in a shaking water bath at 150 oscillation/minute for two hours. The final assay volume was 1.0 ml. After incubation the reaction was stopped by the addition of 1.0 ml of 15% KOH in ethanol, and the internal standard $^3$H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. The compound of Example 1G inhibited 45% of cholesterol synthesis in the non-fasted rats, and that of Example 2E showed 53% inhibition.

What is claimed is:

1. A compound of the formula

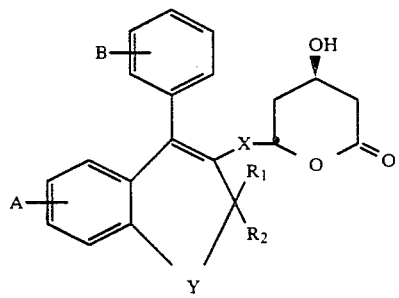

wherein:
A is H, alkyl or alkoxy;
B is H, alkyl, alkoxy, halo or CF$_3$;
X is CH$_2$CH$_2$ or CH=CH
Y is CH$_2$, CH$_2$CH$_2$ or CH=CH
R$_1$ and R$_2$ are independently H, alkyl, hydroxyalkyl, halo or CF$_3$;
or a pharmaceutically acceptable salt thereof.

2. A pharmaceutical composition comprising a therapeutically effective amount of a compound of claim 1 and a pharmaceutically acceptable carrier.

3. The pharmaceutical composition of claim 2 wherein said compound is selected from the group consisting of:
Trans-(E)-6-[2-[5,6-dihydro-7,7-dimethyl-9-(4-fluorophenyl)-7H-benzocyclohepten-8-yl]ethenyl]-4-hydroxy-3,4,5,6-tetrahydro-2H-pyran-2-one;
Trans-(E)-6-[2-[7,7-dimethyl-9-(4-fluorophenyl)-7H-benzocyclohepten-8-yl]ethenyl]-4-hydroxy-3,4,5,6-tetrahydro-2H-pyran-2-one;
Trans-(E)-6-[2-[7,7-dimethyl-9-(3-methyl-4-fluorophenyl)-7H-benzocyclohepten-8-yl]ethenyl]-4-hydroxy-3,4,5,6-tetrahydro-2H-pyran-2-one; and
Trans-(E)-6-[2-[7,7-dimethyl-3-methoxy-9-(3-methyl-4-fluorophenyl)-7H-benzocyclohepten-8-yl]ethenyl]-4-hydroxy-3,4,5,6-tetrahydro-2H-pyran-2-one.

4. The pharmaceutical composition of claim 2 wherein said compound is selected from the group consisting of:
Trans-(E)-6-[2-[7,7-dimethyl-9-(3,5-dimethylphenyl)-7H-benzocyclohepten-8-yl]ethenyl]-4-hydroxy-3,4,5,6-tetrahydro-2H-pyran-2-one;
Trans-(E)-6-[2-[5,6-dihydro-7,7-dimethyl-9-(3-methyl-4-fluorophenyl)-7H-benzocyclohepten-8-yl]ethenyl]-4-hydroxy-3,4,5,6-tetrahydro-2H-pyran-2-one;
Trans-6-[2-[7,7-dimethyl-9-(3-methyl-4-fluorophenyl)-7H-benzocyclohepten-8-yl]ethyl]-4-hydroxy-3,4,5,6-tetrahydro-2H-pyran-2-one; and
Trans-(E)-6-[2-[4,7,7-trimethyl-9-(3-methyl-4-fluorophenyl)-7H-benzocyclohepten-8-yl]ethenyl]-4-hydroxy-3,4,5,6-tetrahydro-2H-pyran-2-one.

5. A method of inhibiting cholesterol biosynthesis in a patient in need of such treatment comprising administering to said patient a pharmaceutical composition defined in claim 2.

* * * * *